(12) United States Patent
Kneale et al.

(10) Patent No.: US 8,033,281 B2
(45) Date of Patent: Oct. 11, 2011

(54) MODULAR TRANSPORTABLE LIFE SUPPORT DEVICE

(76) Inventors: Todd Douglas Kneale, Brea, CA (US); Steven Bruce Alexander, Rolling Hills Estates, CA (US); Terrance Paul Domae, Cerritos, CA (US); John William Quillen, Ontario (CA); Richard Anthony Bongiovanni, Huntington Beach, CA (US); Peter Andrew Barnett, Costa Mesa, CA (US)

( * ) Notice: Subject to any disclaimer, the term of this patent is extended or adjusted under 35 U.S.C. 154(b) by 430 days.

(21) Appl. No.: 11/983,673

(22) Filed: Nov. 9, 2007

(65) Prior Publication Data

US 2009/0119834 A1    May 14, 2009

(51) Int. Cl.
*A61G 15/00* (2006.01)
*A61F 5/37* (2006.01)
*A47B 1/00* (2006.01)

(52) U.S. Cl. ............................. 128/845; 128/870; 5/625

(58) Field of Classification Search .................. 128/845, 128/846, 847, 870, 869; 5/626, 625, 600, 5/81.1, 620, 621, 622, 628, 658, 503.1, 419, 5/420, 627, 624, 656; 600/300
See application file for complete search history.

(56) References Cited

U.S. PATENT DOCUMENTS

| | | | |
|---|---|---|---|
| 117 | A | 7/1915 | Walford |
| 1,200,852 | A | 10/1916 | Kern |
| 1,256,219 | A | 2/1918 | Freedman et al. |
| 1,258,694 | A | 3/1918 | Miller |
| 1,287,855 | A | 12/1918 | Brand |
| 2,401,230 | A | 5/1946 | Colley |
| 2,704,989 | A | 3/1955 | Konecny |
| 2,837,778 | A | 6/1958 | Kern |
| 3,050,331 | A | 8/1962 | Mansen |
| 3,148,911 | A | 9/1964 | Boyer et al. |
| 3,348,245 | A | 10/1967 | Shindler |
| 3,376,059 | A | 4/1968 | Corl |

(Continued)

FOREIGN PATENT DOCUMENTS

EP    0002274    6/1979

(Continued)

OTHER PUBLICATIONS

Aeromed Systems, Inc., Specification / AMT 300, undated, 1 page, Fargo, North Dakota.

(Continued)

*Primary Examiner* — Patricia Bianco
*Assistant Examiner* — Ophelia Hawthorne
(74) *Attorney, Agent, or Firm* — Stetina Brunda Garred & Brucker

(57) ABSTRACT

There is provided a patient care and treatment platform that is connectable to a plurality of modules capable of providing medical functionality. The platform includes a housing and a patient support surface. The platform also includes a power receiver for receiving power. The platform further includes a module interface including power, data, and pneumatic spines having power data and pneumatic ports, respectively. The spines are operative to transfer data, power, and fluid within the platform. The ports are connectable to the modules to integrate the modules into the platform. The platform also includes a head fairing having a patient interface panel. The head fairing includes an inner surface that is substantially concave in shape and slopes away from the patient support surface to allow access to the head of a patient. The patient interface panel includes a plurality of ports connectable to electrical and pneumatic apparatus.

26 Claims, 11 Drawing Sheets

U.S. PATENT DOCUMENTS

| | | | |
|---|---|---|---|
| 3,492,042 | A | 1/1970 | Nachtigall, Jr. |
| 3,531,151 | A | 9/1970 | Branfield |
| 3,678,921 | A | 7/1972 | Brendgord et al. |
| 3,761,968 | A | 10/1973 | Besler |
| 3,775,782 | A | 12/1973 | Rice et al. |
| 3,840,265 | A | 10/1974 | Stirling et al. |
| 3,877,427 | A | 4/1975 | Alexeev et al. |
| 4,003,378 | A | 1/1977 | Pickering |
| 4,034,740 | A | 7/1977 | Atherton et al. |
| 4,060,079 | A | 11/1977 | Reinhold, Jr. |
| 4,079,728 | A | 3/1978 | Gatts |
| 4,161,172 | A | 7/1979 | Pickering |
| 4,224,936 | A | 9/1980 | Cox |
| 4,347,635 | A | 9/1982 | Eisenhauer |
| 4,352,991 | A | 10/1982 | Kaufman |
| 4,425,978 | A | 1/1984 | Star |
| 4,485,806 | A | 12/1984 | Akers |
| 4,584,989 | A | 4/1986 | Stith |
| 4,680,790 | A | 7/1987 | Packard et al. |
| 4,715,385 | A | 12/1987 | Cudahy et al. |
| 4,724,844 | A | 2/1988 | Rafelson |
| 4,747,172 | A | 5/1988 | Hohol et al. |
| 4,757,811 | A | 7/1988 | Clark |
| 4,768,241 | A | 9/1988 | Beney |
| 4,780,919 | A | 11/1988 | Harrison |
| 4,783,109 | A | 11/1988 | Bucalo |
| 4,957,121 | A | 9/1990 | Icenogle et al. |
| 4,981,139 | A | 1/1991 | Pfohl |
| 5,005,230 | A | 4/1991 | Congdon |
| 5,016,307 | A | 5/1991 | Rebar |
| 5,020,546 | A | 6/1991 | Russo |
| 5,034,181 | A | 7/1991 | Billiu |
| 5,050,254 | A | 9/1991 | Murphy |
| 5,063,924 | A | 11/1991 | Galvan et al. |
| 5,077,843 | A | 1/1992 | Dale et al. |
| 5,084,922 | A | 2/1992 | Louit |
| 5,092,722 | A | 3/1992 | Reazer, III et al. |
| 5,111,818 | A | 5/1992 | Suzuki et al. |
| 5,117,521 | A | 6/1992 | Foster et al. |
| 5,121,514 | A | 6/1992 | Rosane |
| 5,149,030 | A | 9/1992 | Cockrill |
| 5,173,142 | A | 12/1992 | Billiu |
| 5,229,052 | A | 7/1993 | Billiu |
| 5,236,390 | A | 8/1993 | Young |
| 5,306,026 | A | 4/1994 | Jesse |
| 5,307,818 | A | 5/1994 | Segalowitz |
| 5,316,542 | A | 5/1994 | Koch et al. |
| 5,331,549 | A | 7/1994 | Crawford, Jr. |
| 5,331,991 | A | 7/1994 | Nilsson |
| 5,335,651 | A | 8/1994 | Foster et al. |
| 5,338,588 | A | 8/1994 | Billiu |
| 5,342,121 | A | 8/1994 | Koria |
| 5,404,877 | A | 4/1995 | Nolan et al. |
| 5,421,340 | A | 6/1995 | Stanga et al. |
| 5,441,047 | A | 8/1995 | David et al. |
| 5,474,574 | A | 12/1995 | Payne et al. |
| 5,494,051 | A * | 2/1996 | Schneider, Sr. ............ 5/625 |
| 5,497,766 | A | 3/1996 | Foster et al. |
| 5,511,553 | A | 4/1996 | Segalowitz |
| 5,570,483 | A | 11/1996 | Williamson |
| 5,579,001 | A | 11/1996 | Dempsey et al. |
| 5,590,648 | A | 1/1997 | Mitchell et al. |
| 5,615,430 | A | 4/1997 | Nambu et al. |
| 5,626,151 | A | 5/1997 | Linden |
| 5,630,238 | A | 5/1997 | Weismiller et al. |
| 5,646,462 | A | 7/1997 | Cortes et al. |
| 5,664,270 | A | 9/1997 | Bell et al. |
| 5,680,661 | A | 10/1997 | Foster et al. |
| 5,687,717 | A | 11/1997 | Halpern et al. |
| 5,749,374 | A | 5/1998 | Schneider, Sr. |
| 5,781,422 | A | 7/1998 | Lavin et al. |
| 5,782,244 | A * | 7/1998 | Kostich ............ 128/869 |
| 5,783,964 | A | 7/1998 | Eitan |
| 5,801,931 | A | 9/1998 | Kino et al. |
| 5,853,361 | A | 12/1998 | Kobayashi et al. |
| 5,975,081 | A * | 11/1999 | Hood et al. ............ 128/845 |
| 6,001,057 | A | 12/1999 | Bongiovanni et al. |
| 6,017,307 | A * | 1/2000 | Raines ............ 600/300 |
| 6,175,977 | B1 * | 1/2001 | Schumacher et al. ............ 5/626 |
| 6,182,667 | B1 | 2/2001 | Hanks et al. |
| 6,230,710 | B1 | 5/2001 | Sobko et al. |
| 6,234,172 | B1 * | 5/2001 | Ausbourne et al. ............ 128/845 |
| 6,282,094 | B1 | 8/2001 | Lo et al. |
| 6,525,942 | B2 | 2/2003 | Huang et al. |
| 7,253,503 | B1 | 8/2007 | Fusaro et al. |

FOREIGN PATENT DOCUMENTS

| | | |
|---|---|---|
| EP | 0707867 | 4/1996 |
| FR | 1373384 | 11/1962 |
| GB | 0000117 | 7/1915 |
| GB | 1473862 | 3/1974 |
| GB | 1416697 | 12/1975 |
| GB | 1473862 | 5/1977 |
| JP | 62122664 | 6/1987 |
| JP | 6323665 | 11/1994 |
| WO | WO9401023 | 1/1994 |
| WO | PCT/AU95/00477 | 8/1995 |

OTHER PUBLICATIONS

Mobile Intensive Care Rescue Facility (MIRF), undated, 16 pages.
MOBI: Mobile Intensive Care Unit, Innovation in Critical Care Patient Transport, undated, 2 pages.
Buchanan Aircraft Corporation, (M.I.R.F.) Mobile Intensive Care Rescue Facility, undated, 17 pages, Queensland, Australia.
Spectrum Aeromed, Above and Beyond, undated, 14 pages, Wheaton, MN, USA.
LifePort, Inc., The Results of Innovation, undated, 30 pages, Vancouver, WA, USA.

* cited by examiner

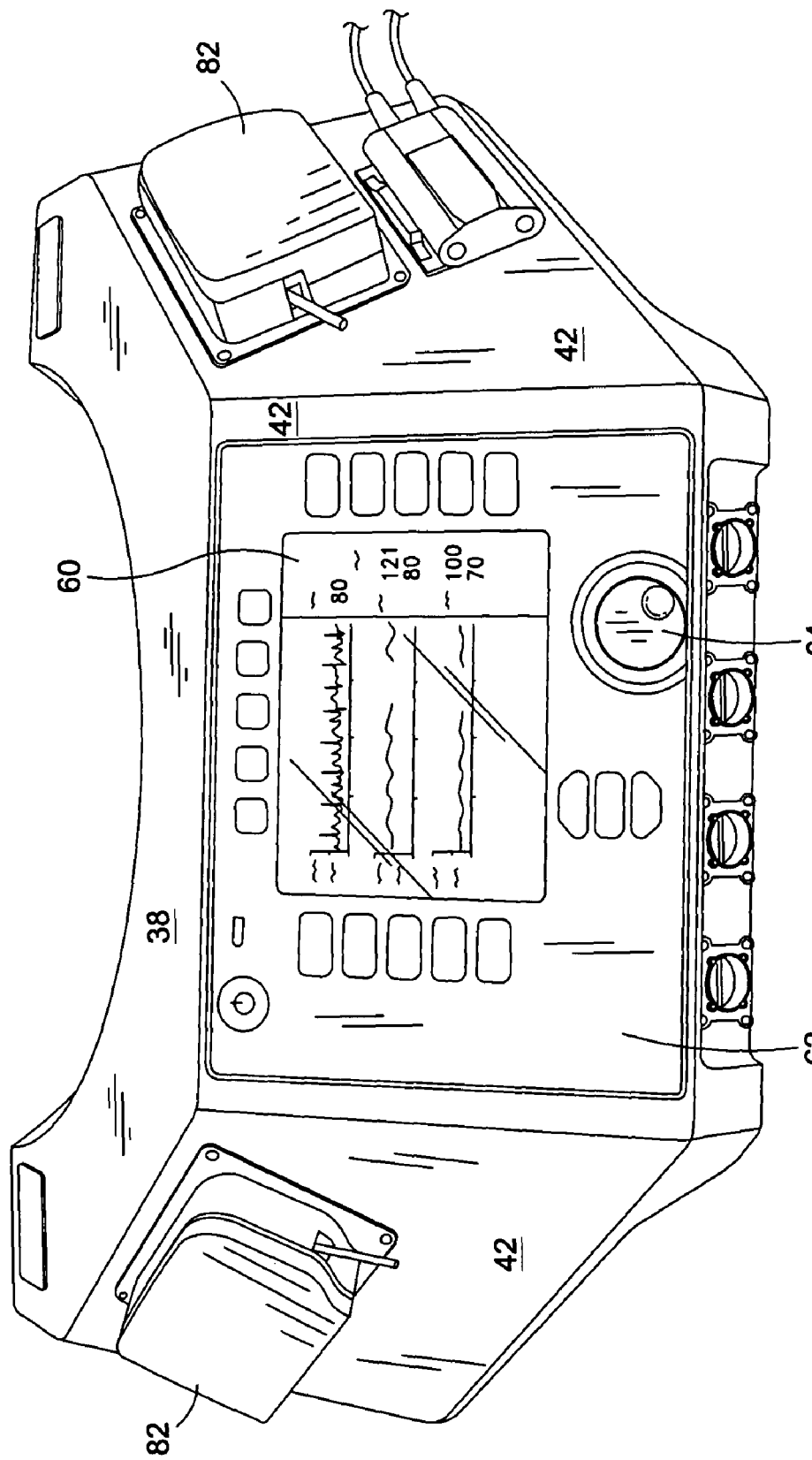

US 8,033,281 B2

MODULAR TRANSPORTABLE LIFE SUPPORT DEVICE

CROSS-REFERENCE TO RELATED APPLICATIONS

Not Applicable

STATEMENT RE: FEDERALLY SPONSORED RESEARCH/DEVELOPMENT

Not Applicable

BACKGROUND

The present invention relates to portable medical treatment systems, including a plurality of patient monitoring/treatment devices. More particularly, the invention relates to a patient care and treatment device capable of hosting a suite of medical monitoring/treatment modules useful to treat a patient and adaptable to function in various environments, including full service hospitals, field stations or in medical transport.

Many people suffer from injury and disease and require immediate medical attention. In many cases, an emergency response team is called to the patient's location for transport to a medical facility. The emergency response team may begin diagnosing and treating the patient for his injury or disease while en route. Although such a medical response is sufficient in most civilian applications, there may be extreme situations in which a traditional response is insufficient.

In the case of natural disasters and battlefield environments, patients may be located in remote, hard to reach locations. As such, lightweight, portable medical equipment is a high priority in order to provide prompt medical treatment and therapy. In addition, it may be necessary to carry the patient from the remote location to an evacuation vehicle for transport to a medical facility.

In other less hazardous environments, it is also useful to have portable medical devices that can easily be brought into use where the demand for medical attention may be beyond the levels that are supported by the number of dedicated operating or critical care rooms. Such cases may arise, for example, where a local hospital receives a large number of patients as a result of a transportation accident, or where the normal demands progressively increase beyond the existing capacity of a medical facility. As such, portable suites of medical monitoring/treatment devices are suitable for an expanding number of applications, both for emergency services and otherwise.

Contemporary medical response devices have typically included patient support platforms having an array of substantially off the shelf medical monitoring/treatment devices secured to or supported by the platform. In most cases such devices operate independently of each other, which is useful in minimizing the expense of integration and obtaining necessary approvals for marketing of such devices without the need for government certification of systems including devices substantially modified from their already approved condition.

However, while such contemporary systems offer certain economic advantages in reduced development costs, the resulting systems would likely suffer from many short-comings, such as wiring demands, difficulty in implementing simultaneous control over multiple functions, difficulties in supporting updates in various monitoring/treatment devices without modifying central processing and power distribution functions, and other factors affecting the simplicity, reliability and stability of the overall platform. Additionally, doctors and nurses may well find it easier to perform medical procedures using integrated displays and controls, rather than an array of separately functioning devices that may each have their own unique operational requirements, user interfaces and space requirements that may prove challenging to the medical personnel treating the patient.

It is further useful if such improvements to existing suites of medical monitoring/treatment devices can be implemented in a manner that facilitates environmental support of the patient and the devices, in a manner that is readily tailorable to the presence and location of medical monitoring/treatment modules, and the individual requirements thereof.

The present invention addresses the above requirements. As described more fully below, the present invention, in its various inventive aspects, provides a structure, architecture, and systems which cooperate to provide an integrated, reliable, multi-function suite of integrated devices that can be useful to implement a variety of medical functions and regimens that provide a high degree of patient support with a user friendly display and interface. As such, the present invention allows the extension of quality medical treatment to many applications where more rudimentary support was typically available.

BRIEF SUMMARY

According to an aspect of the present invention, there is provided a patient care and treatment platform being connectable to a plurality of medical modules. Each medical module is capable of providing discrete medical functionality. The platform includes a housing having a head portion and a foot portion. A patient support further includes a control spine connected to the housing. The control spine includes a control unit and a plurality of control ports. Each control port is configured to enable selective attachment/detachment to a respective one of the plurality of medical modules to enable centralized control over the plurality of modules. The control unit is configured to transmit communications along the control spine, which may ultimately be received by the plurality of modules. The platform additionally includes a patient interface panel having a plurality of treatment ports. Each treatment port is connectable with a respective one of the plurality of medical modules and a medical monitoring/treatment apparatus.

It is contemplated that the control spine may be configured to communicate power, data, and/or fluid therealong. With regard to power transfer, the control spine may be in electrical communication with a power source to enable the platform to communicate power to the modules. In addition, the control spine may be configured to facilitate data communication between the modules and the platform. Furthermore, the control spine may be configured to enable fluid transfer thereal-ong. In this regard, a fluid source may be in fluid communication with the control spine.

The present invention provides a portable suite of medical functionality for emergency response situations integrated into a single platform capable of enabling centralized operation and control over the integrated units. The central power, data, and/or pneumatic capabilities of the control spine provide power, data and pneumatic transfer as required by the modules. The modular architecture enables high flexibility and adaptability with regard to the medical functionality provided by the present invention.

Other aspects of the present invention may also include a housing that includes a head fairing. The head fairing includes bottom, top, inner and outer surfaces. The inner surface extends between the top and bottom surfaces and may be generally concave in shape and slopes away from the patient support surface. An end surface is disposed between the bottom, top, inner and outer surfaces. A patient interface panel may be disposed on the head fairing.

The platform may further include an environmental control unit to control the temperature within the housing. The environmental control unit may include a temperature sensor to monitor the temperature within the housing and an environmental control circuit in electrical communication with the temperature sensor. A fan may be in electrical communication with the environmental control circuit. The fan may be operative to force air-flow within the housing to control the temperature within the housing. The fan may be responsive to operational instructions communicated from the environmental control circuit.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 3A is a cutaway view of the platform shown in FIG. 3 showing a plurality of modules connected to a module interface;

FIG. 5 is a top perspective view of the head fairing of FIG. 4, wherein the head fairing has been rotated 180 degrees;

DETAILED DESCRIPTION

Figure 1:
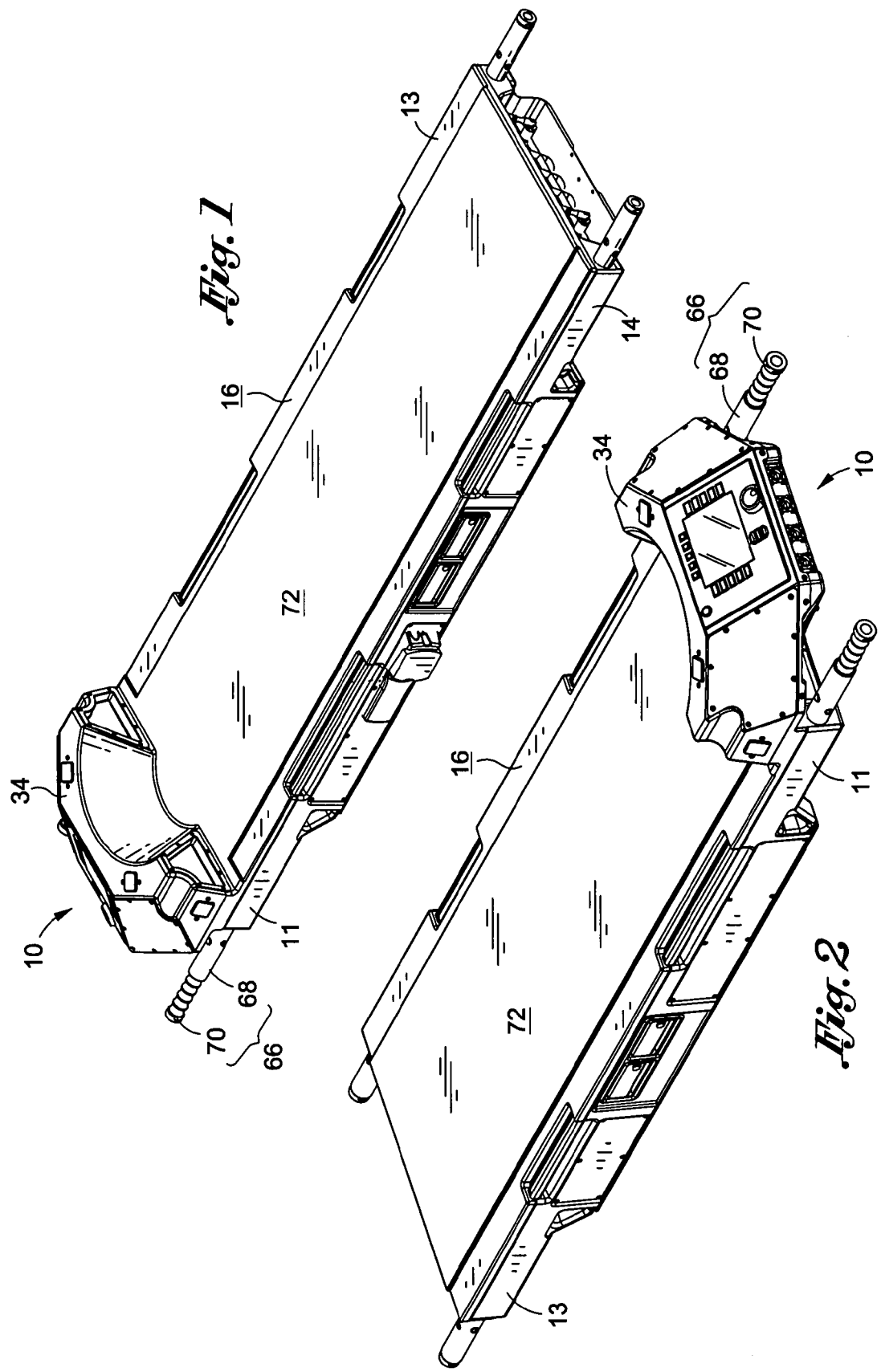
FIG. 1 is a top perspective view of a patient care and treatment platform including a housing having a head fairing and a patient support surface disposed on the housing.

Set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

Referring now to FIGS. 1-12 and according to an embodiment of the present invention, there is provided a patient care and treatment platform 10 configured to provide centralized operation and control capabilities for a plurality of modular medical units. The platform 10 includes a housing 14 and a patient support surface 16 disposed thereon. The platform housing 14 may include a head portion 11 and a foot portion 13. The patient support surface 16 is generally planar and is capable of supporting a patient. It is contemplated that the patient support surface 16 will accommodate patients of varying size. However, various extensions may be added to provide additional support. For instance, in the case of a very tall patient, a foot extension may be connected to the patient support surface 16 to provide additional support. Certain embodiments of the invention may include a comfort pad 72 disposed on the patient support surface 16 to provide additional comfort for a patient resting thereon.

The platform 10 is configured to integrate various medical functionalities into a single portable unit. To this end, the platform 10 enables selective attachment/detachment to a plurality of medical modules 12. Each module 12 is a sealed unit which contains discrete medical functionality (e.g. physiological monitoring, infusion, blood chemistry, ventilation, suction, etc.). Therefore, the platform 10 may enable high portability and adaptability so as to allow high-level medical response in remote locations or extreme conditions. For instance, the platform 10 may be configured to support resuscitation, stabilization and transport of adult and pediatric trauma victims or patients needing physiological monitoring and treatment capabilities of a hospital intensive care unit or trauma care unit for pre-operative, intra-operative and post-operative support during pre-, intra-, and post-transport phases. In general, use of the present invention may be anticipated for victims of combat/civilian casualty, trauma, respiratory distress, pneumothroax, severe fluid loss, cardiac emergency or unstable clinical presentation. A deployed platform 10 provides a portable, individualized ICU and the supporting equipment and communications to assess, treat and evacuate the trauma casualty from the point of injury to facilities providing more definitive health care.

It is contemplated that the modules 12 include medical devices 110 capable of performing various medical treatment and monitoring functions. Such treatment and monitoring functions may include, but is not limited to a clinical analyzer, a defibrillator, infusion pumps, suction/aspiration, ventilation, $CO_2O_2$ flow, Oxygen generator, Oxygen gas router, and physiological monitoring, including electrocardiograph, non-invasive blood pressure, heart rate, pulse oximetry, invasive blood pressure, core temperature, and non-invasive respiratory rate. In one embodiment, the medical devices 110 included within each module 12 may include original equipment manufacture (OEM) medical devices 110.

The platform 10 includes a centralized operation and control system which enables integration of a plurality of medical modules 12. In particular, the centralized operation and control system includes a central control spine 15 connected to the housing 14, as best illustrated in FIG. 3A. The control spine 15 includes a plurality of control ports and a control unit 90 configured to transmit communications along the control spine 15. The control ports may include power ports 24, data ports 28, and/or pneumatic ports 32 to facilitate power, data, and/or pneumatic communication between the control spine 15 and the modules 12, respectively. The control ports are configured to enable selective attachment/detachment of the modules 12 to the platform 10. In this regard, the medical capability of the platform 10 may be adapted to the particular needs of the patient by adding or removing modules 12. One aspect of the present invention includes a standard module size (e.g. 1U, 2U, 3U, etc) and packaging approach taking into consideration environmental factors such as shock, and vibration, as well as common medical device safety issues including isolation, and electromagnetic compatibility, and external packaging volumes. A standard module size enables quick and easy modifications to the medical functionality of the platform 10.

According to various embodiments of the invention, there are provided a number of accessories which may be added to the platform 10 for customization for a particular treatment or patient. One embodiment includes a rail system which enables a user to attach various accessories to the platform 10. Such accessories may include, but is not limited to, patient positioning accessories, an IV pole, a Forward Surgical Team (FST) operating table rail and accessories, arm boards, patient positioning pads, and head/foot board patient surface extensions. The platform 10 may further include patient restraints 84 to secure the patient to the platform 10.

According to one embodiment, the platform 10 is man-portable and weigh less than 120 lbs. The relative light weight of the platform 10 enables quick and easy transport thereof. The platform 10 may be used to carry a patient from a remote location to an evacuation vehicle for transport to a medical facility. As such, in one embodiment of the invention, the platform 10 fits into the litter stanchions for various water, land, and air evacuation vehicles.

Figure 2:
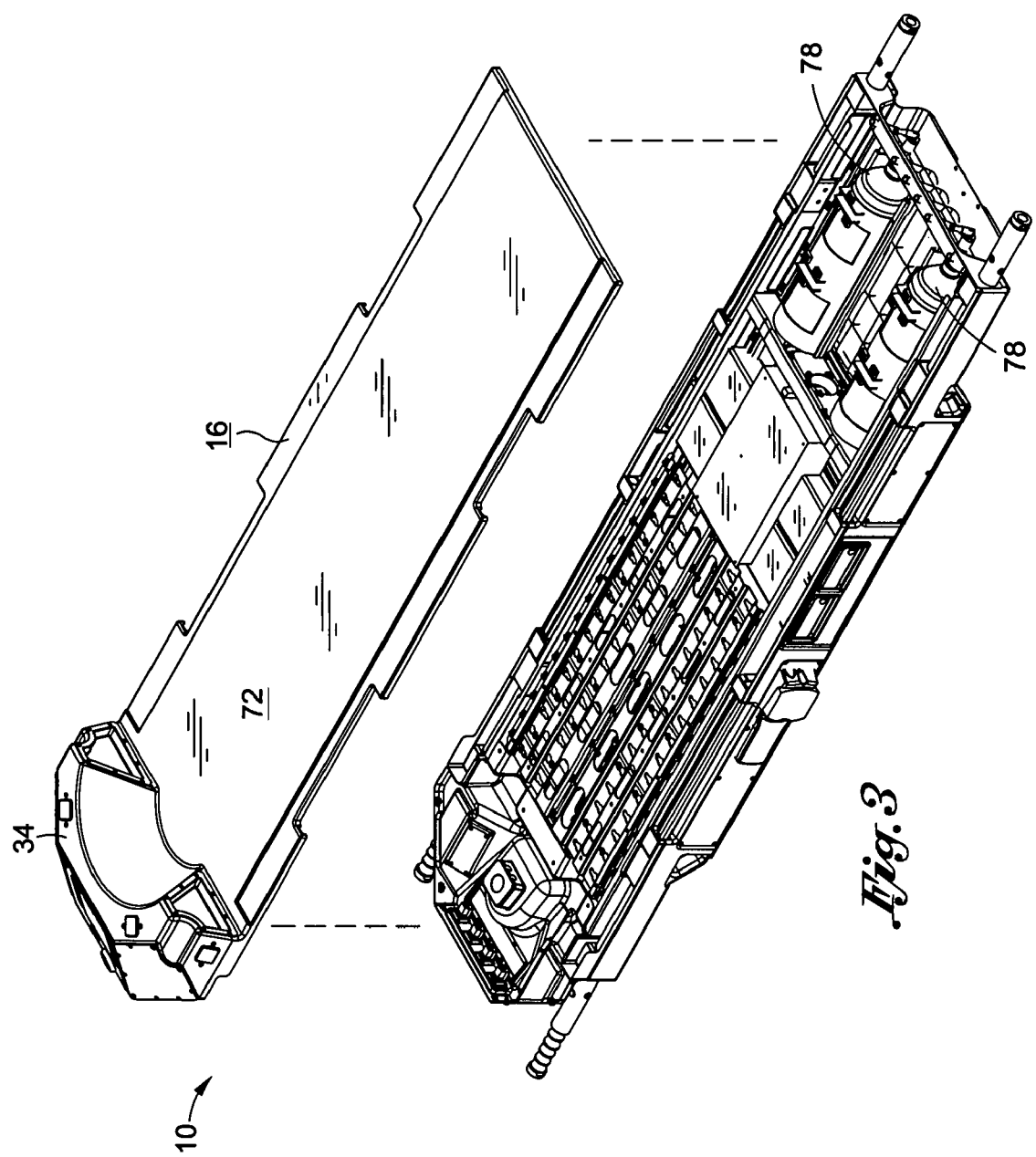
FIG. 2 is a top perspective view of the patient care and treatment platform of FIG. 1, wherein the platform has been rotated 180 degrees.
Figure 3:
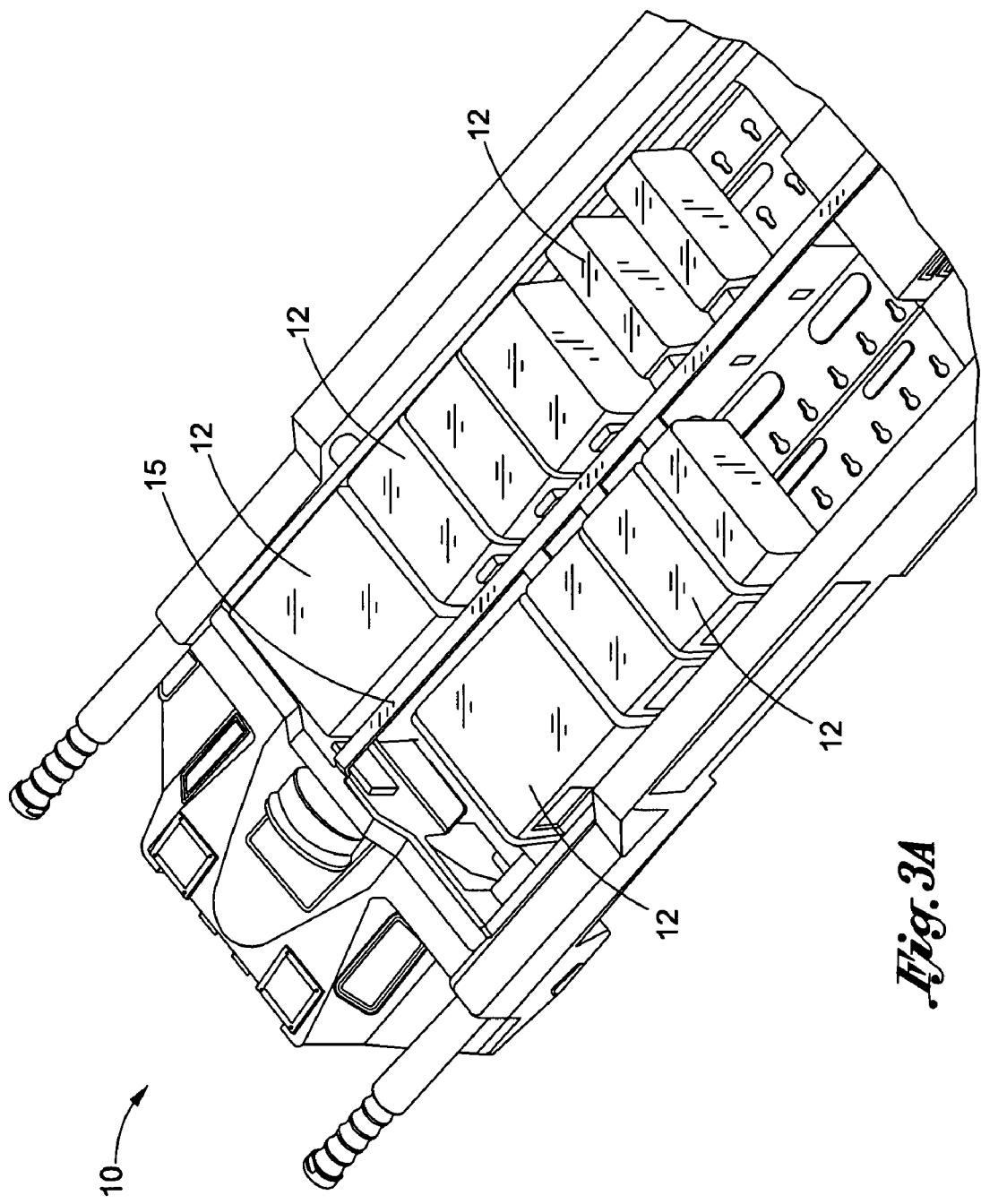
FIG. 3 is an exploded view of the patient care and treatment platform, wherein the platform includes an internal oxygen source disposed within the platform for supplying oxygen to a patient.

The platform 10 may also include handles 66 to facilitate carrying of the platform 10. As shown in FIGS. 1 and 2, the platform 10 includes four handles 66 with one handle 66 located at each corner of the platform 10 to allow two, three, or four men to carry the platform 10. The handles 10 may include a receptacle portion 68 and a body portion 70, where the body portion 70 is retractable into the receptacle portion 68. As shown in FIGS. 1 and 2, the handles 66 located at the foot portion 11 of the housing 14 are retracted into the receptacle portion 68, whereas the handles 66 located on the head portion 13 are extended.

It is contemplated that certain embodiments of the invention includes a head fairing 34. The head fairing 34 may provide the operator with a centralized interface on the platform 10 without obstructing physical access to the patient. In this regard, the head fairing 34 may display operational information that relates to various procedures being performed on the patient. In addition, the head fairing 34 may provide a connection point for various medical treatment and monitoring apparatus, as described in more detail below.

Figure 4:
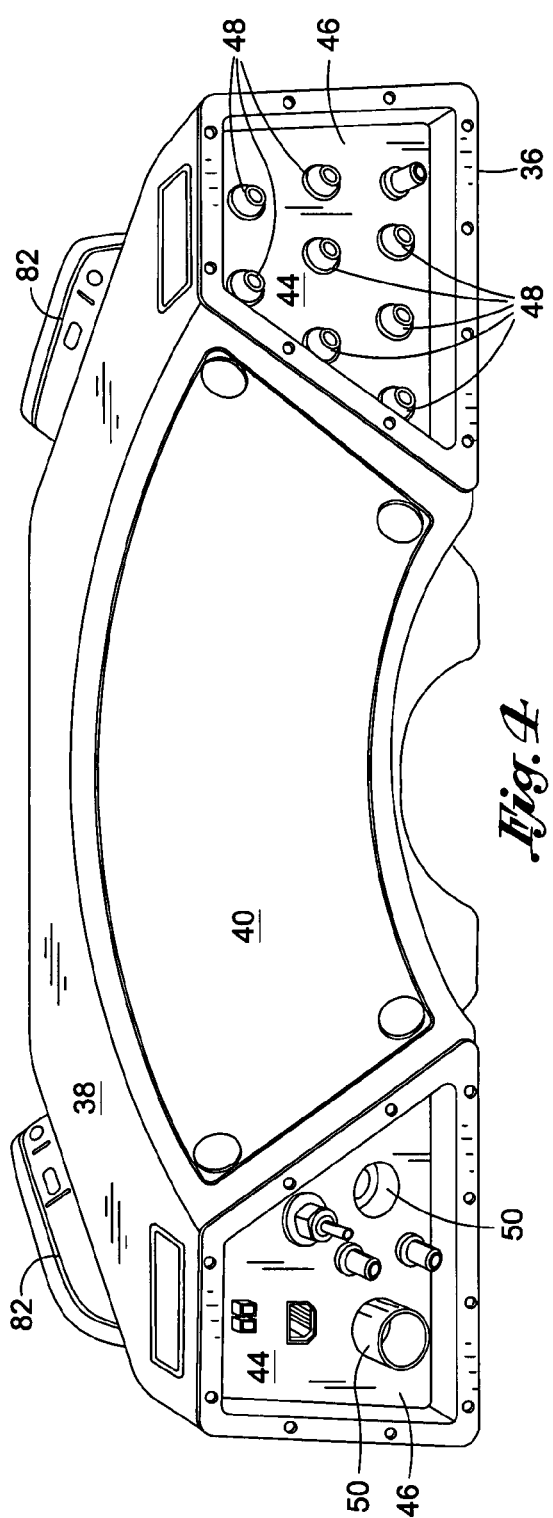
FIG. 4 is a top perspective view of the head fairing.
Figure 6:
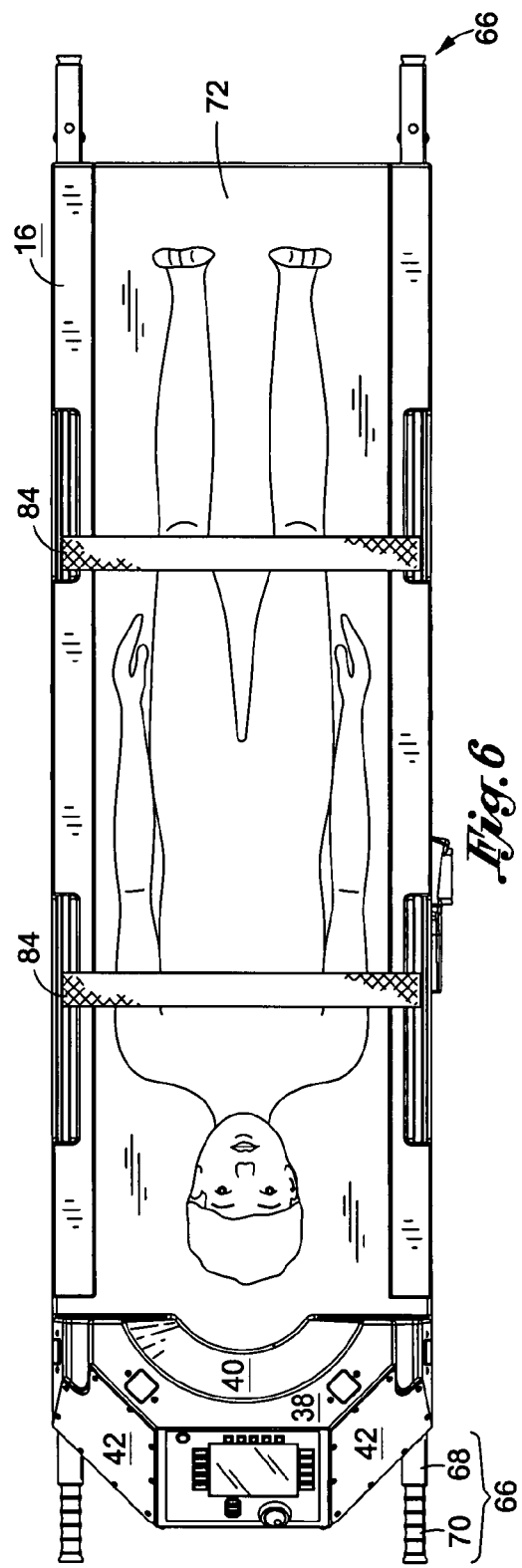
FIG. 6 is a top view of the platform with a patient secured to the patient support surface.
Figure 7:
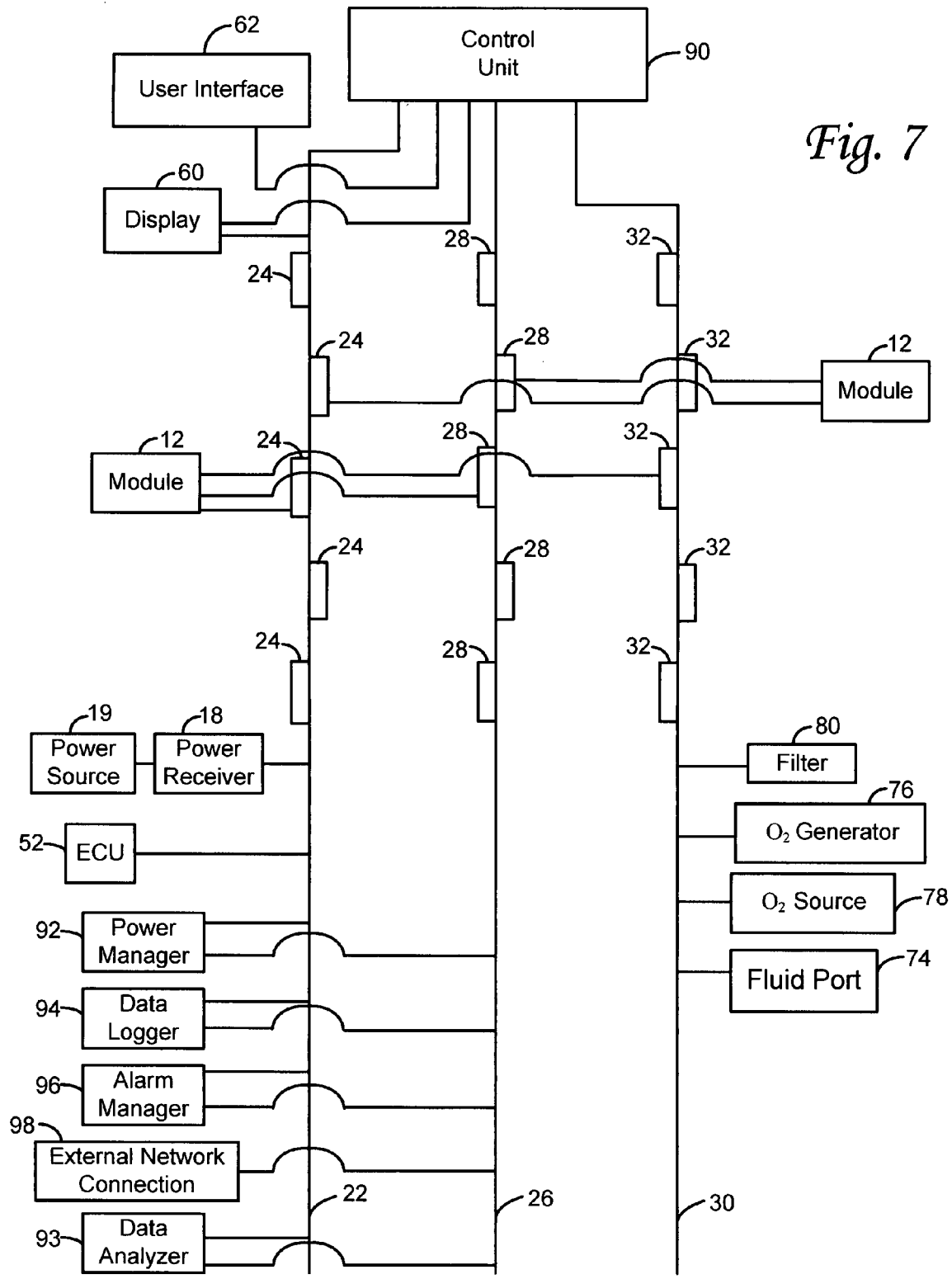
FIG. 7 is a block diagram of a power, data and pneumatic system for the platform, wherein the power, data, and pneumatic systems include a power, data, and pneumatic spine, respectively.

Referring now to FIGS. 4 and 5, the head fairing 34 includes top and bottom surfaces 38, 36, with inner and outer surfaces 40, 42 extending therebetween. An end surface 44 is disposed between the bottom, top, inner, and outer surfaces 36, 38, 40, 42. The inner surface 40 is generally concave in shape and slopes away from the patient support surface 16, as can be seen in FIGS. 1 and 6. In this regard, as a patient rests on the patient support surface 16 with his head resting on the head portion 11, the head fairing 34 wraps around the patient's head, and the inner surface 40 slopes away from the patient. The sloping, concave inner surface 40 enables access to the patient's head for the medical provider.

According to various aspects of the present invention, the head fairing 34 includes an assortment of attachments and interface panels, as best shown in FIGS. 4 and 5, which may vary depending upon module 12 configuration. One embodiment of the head fairing 34 includes a patient interface panel 46 disposed on the head fairing 34. However, it is understood that the patient interface panel 46 may be connected to other portions of the housing 14. In addition, the patient interface panel 46 may also be directly connected to a module 12. The patient interface panel 46 provides a connection point for patient apparatus. As used herein, a patient apparatus is the physical tool or instrument that interacts with the patient. For instance, in the case of a defibrillator, the patient apparatus includes the defibrillator paddles. It is contemplated that the patient apparatus may require an electrical or pneumatic connection at the patient interface panel 46.

A patient apparatus requiring an electrical connection is referred to as an electrical apparatus. Each electrical apparatus is connectable to a treatment port 48 disposed on the patient interface panel 46. An electrical apparatus receives signals/data from a patient and communicates that information to a respective one of the plurality of modules 12. In this regard, the treatment port 48 enables electrical communication between the electrical apparatus and a respective one of the medical modules 12. The treatment port 48 may in direct electrical communication with a given module 12, or the treatment port 48 may communicate with the module 12 via the control spine 15.

A patient apparatus requiring a pneumatic connection is referred to as pneumatic apparatus. Pneumatic apparatus are connectable to pneumatic ports 50 disposed on the patient interface panel 46. When connected, the pneumatic apparatus is in fluid communication with a respective one of the plurality of modules 12. The pneumatic ports 50 may be in direct fluid communication with a module 12, or they may communicate via the control spine 15.

Each pneumatic and treatment apparatus may be configured to connect to a specific pneumatic and treatment port 50, 48, respectively. As such, a particular implementation of the invention will include pneumatic and treatment ports 50, 48 that vary in size to prevent accidental connection of a pneumatic or treatment apparatus to the wrong port. In addition, the pneumatic and treatment ports 50, 48 may be color coordinated to assist a user in finding a corresponding port 50, 48 for the apparatus.

As mentioned earlier, centralized control over the various modules 12 may be achieved through their integration with the platform 10. Such control or operator input over the various functions performed by the platform 10 may be accomplished via a user interface 62. In the embodiment shown in FIG. 5, the user interface 62 is disposed on the head fairing 34. The user interface 62 allows a user to input operational instructions into the control unit 90. As such, the user may input operational instructions according to the specific treatment or therapy that will be performed. The user interface 62 may include a series of knobs and/or buttons to allow the user to input data/commands. In one particular embodiment, a rotary encoder knob 64 with a switch may be the primary navigation instrument. As the knob 64 rotates, the user may navigate through various options, and pushing down on the knob 64 enables the switch to support navigation selection.

The medical functions performed by the platform 10 tend to generate patient data. Therefore, various embodiments of the present invention include a display 60 to communicate the data to the operator. In the embodiment shown in FIG. 5, the display 60 is located on the head fairing 34; however, it is understood that the display 60 may be connected to other portions of the housing 14. The display 60 is in electrical communication with the control spine 15 and receives information therefrom, including, but not limited to power, data, and pneumatic information. In other embodiments of the invention, the display 60 is separate from the platform 10 to enable the presentation of patient data at a remote location.

Such a display 60 may receive patient data via a tethered connection, or via wireless communication. In other embodiments, information may additionally be transferred via a headset interface to allow auditory reception of medical information from the device to a crewman's intercom system or headset.

Certain embodiments of the invention combine the display 60 and the user interface 62, as shown in FIG. 5. The embodiment shown in FIG. 5 includes a rotary knob 64, touch screen and buttons. The touch screen may be the primary display device and secondary input device. In another embodiment, the combined display 60 and user interface 62 includes an LCD screen, an audio speaker, and discrete visual indicators, such as LEDs or lamps as output devices. Further embodiments include push-buttons that are associated with screen information displayed on the LCD.

An integral part of many medical treatments and therapies includes infusion. As such, one embodiment of the head fairing 34 includes an infusion pump 82 to administer such infusion. The infusion pump 82 may be a low rate infusion pump or a high rate infusion pump. In one embodiment, the low rate infusion pump is capable of infusion rates of at least 400 ml per hour, and the high rate infusion pump is capable of infusion rates of at least 6000 ml per hour. In one embodiment, the infusion pumps 82 are in electrical communication with one or more of the plurality of modules 12. In another embodiment, the infusion pumps 82 are in electrical communication with the power spine 22 to receive power therefrom. Additionally, the infusion pumps 82 may be in electrical communication with the control spine 15 to enable communication between the pumps 82 and the control spine 15.

According to one embodiment, the module 12 integration requires connection to the control network 15. Upon such connection, power, data, and fluid transfer between the modules 12 and the platform 10 may be achieved. Therefore, the control spine 15 may include a data spine 26, power spine 22, and/or a pneumatic spine 30. The embodiment shown in FIG. 7 includes power, data and pneumatic spines 22, 26, 30. However, it is understood that several embodiments of the present invention may include various combinations of the power, data and pneumatic spines 22, 26, 30. The following describes the power, data, and pneumatic spines 22, 26, 30 in more detail.

In one embodiment, the control spine 15 includes a power spine 22 connected to the housing 14. The power spine 22 is a central power distributor between a power source 19 and various components of the platform 10, including the modules 12. The power spine 22 includes a plurality of power ports 24 which are connectable to the modules 12. In this regard, the modules 12 can quickly and easily connect to the power spine 22 via the power ports 24. The power spine 22 is additionally in electrical communication with a power receiver 18 which receives power from a power source 19. The power source 19 may provide power in both Alternating Current (AC) and Direct Current (DC). According to various aspects of the invention, the power source 19 may be an internal power source (e.g. a battery) or an external power source. An internal power source is capable of providing power to the platform 10 when deployed in remote locations where external power may be unavailable. The platform 10 may include multiple power receivers 18 within the housing 14 so as to enable connection of multiple power sources 19 to the platform 10. This is particularly important when the platform 10 operates on internal power for long periods of time.

It is contemplated that the internal power sources may be hot-swappable. In this regard, internal power sources may be removed and replaced during normal operation without operational interruption. To optimize the usage of the internal power sources, one internal power source at a time may be utilized to supply power to the power spine 22 until it has been discharged.

Figure 8:
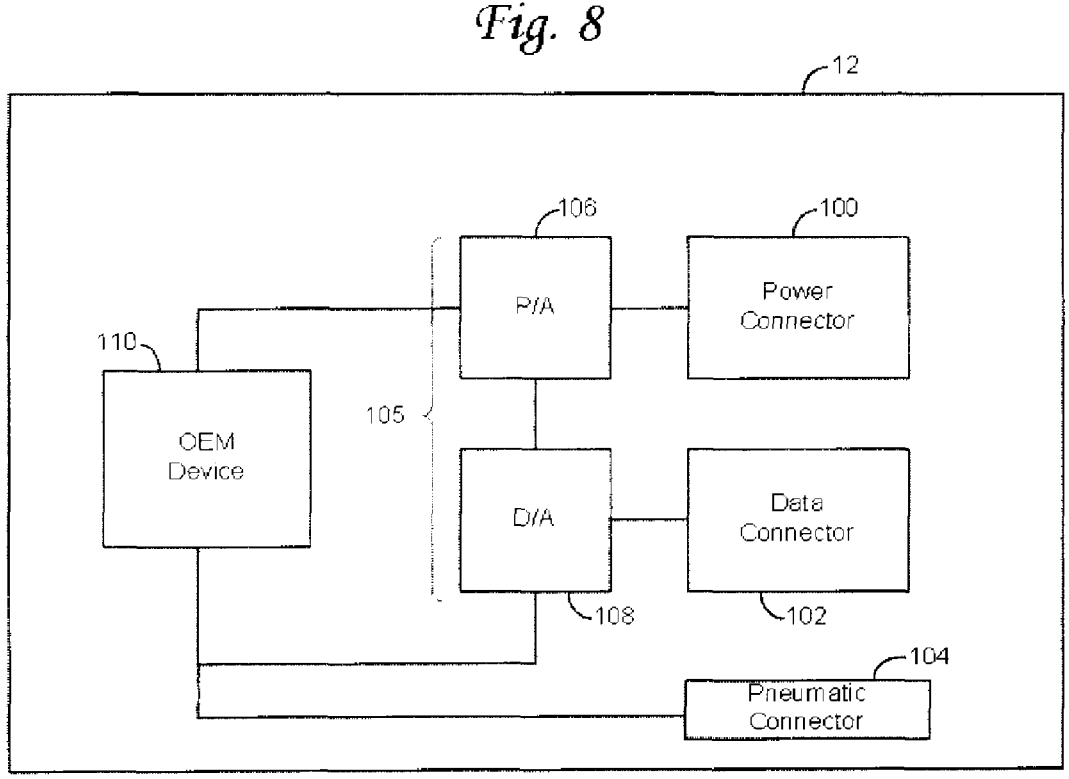
FIG. 8 is a block diagram of a module which is connectable to the power, data, and pneumatic spines illustrated in FIG. 7.
Figure 9:
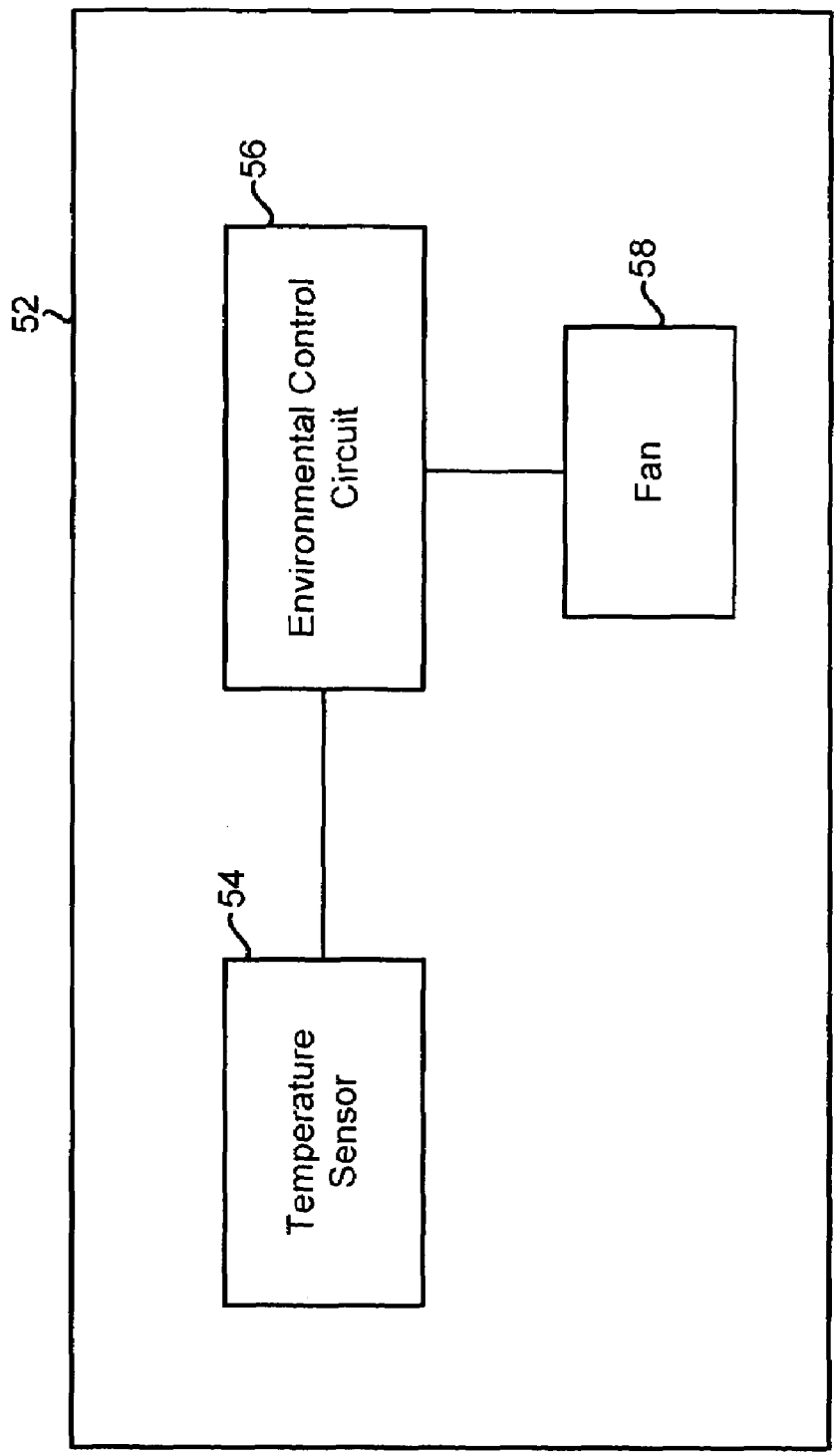
FIG. 9 is a block diagram of an environmental control unit being operative to control the internal temperature of the platform.

As shown in FIG. 8, the modules 12 may include a power connector 100 which connects with a respective one of the plurality of power ports 24 on the power spine 22 to enable power transfer from the power spine 22 to the module 12. It is understood that the power supplied by the power spine 22 may not be acceptable to the specific medical device 110 located within the module 12, especially if the medical device 110 is an OEM device. For instance, power may be supplied by the power spine 22 at a first voltage, and the medical device 110 may require power at a second voltage. Therefore, the module 12 includes a power adapter 106 which receives power from the power spine 22 via the power connector 100 and converts the power according to the power requirements of the medical device 110. In other words, the power adapter 106 converts power from the first voltage into the second voltage. The power adapter 106 enables integration of several medical devices 110 into the power spine 22. Medical devices 110 having power requirements that differ from the power supplied by the power spine 22 may become operable after connection to the power spine 22 because of the power conversion performed by the power adapter 106. When powering down, some modules 12 may require a time period to perform necessary shutdown functions before power is removed. Therefore, according to one embodiment, the power adapter 106 provides the capability to detect the loss of power and to continue to provide power to the module 12 for some period of time as needed to prevent damage or data corruption.

Figure 10:
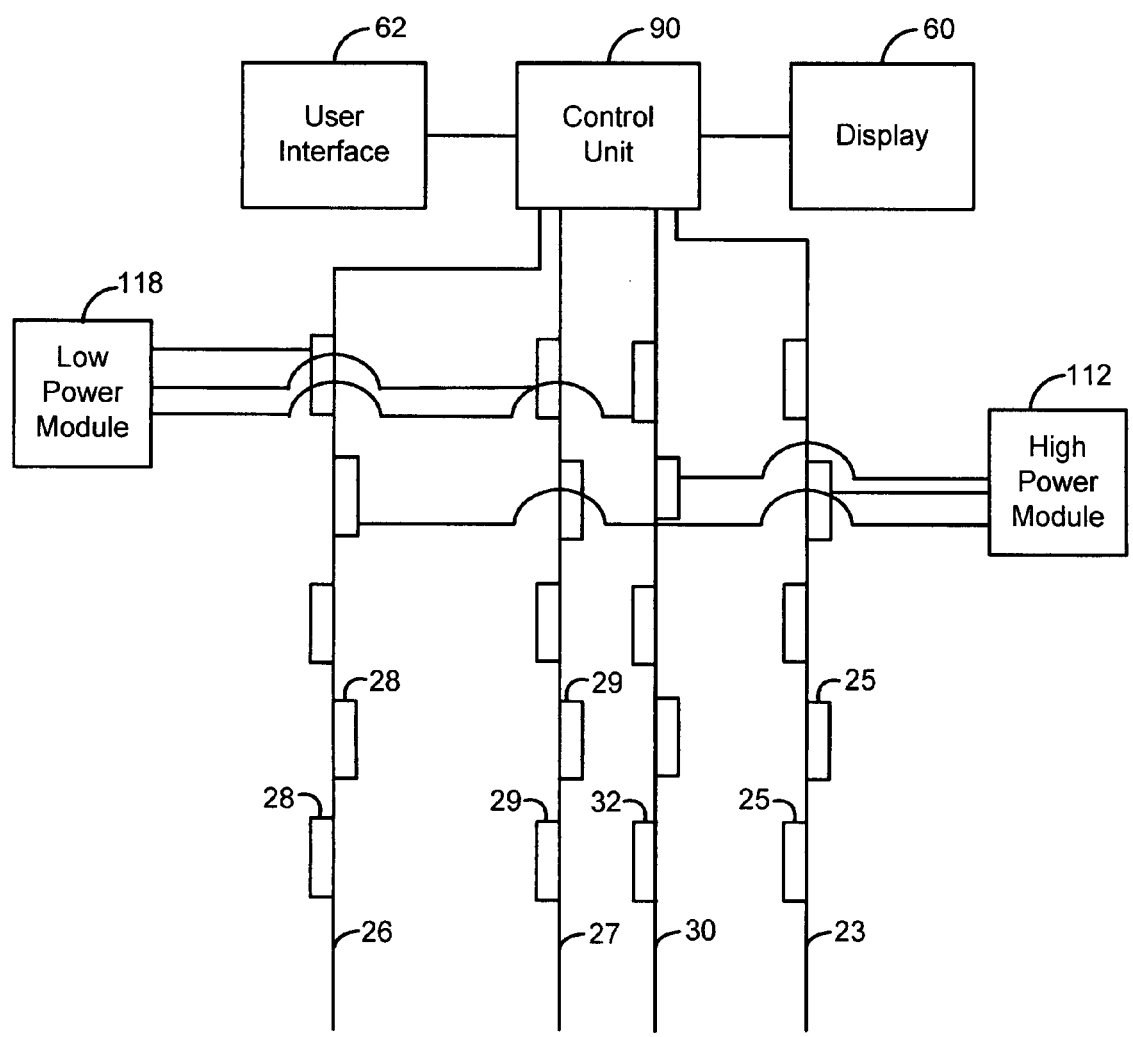
FIG. 10 is a block diagram of an embodiment of the present invention including a high power spine and a lower power spine connectable to high power modules and low power modules, respectively.
Figure 11:
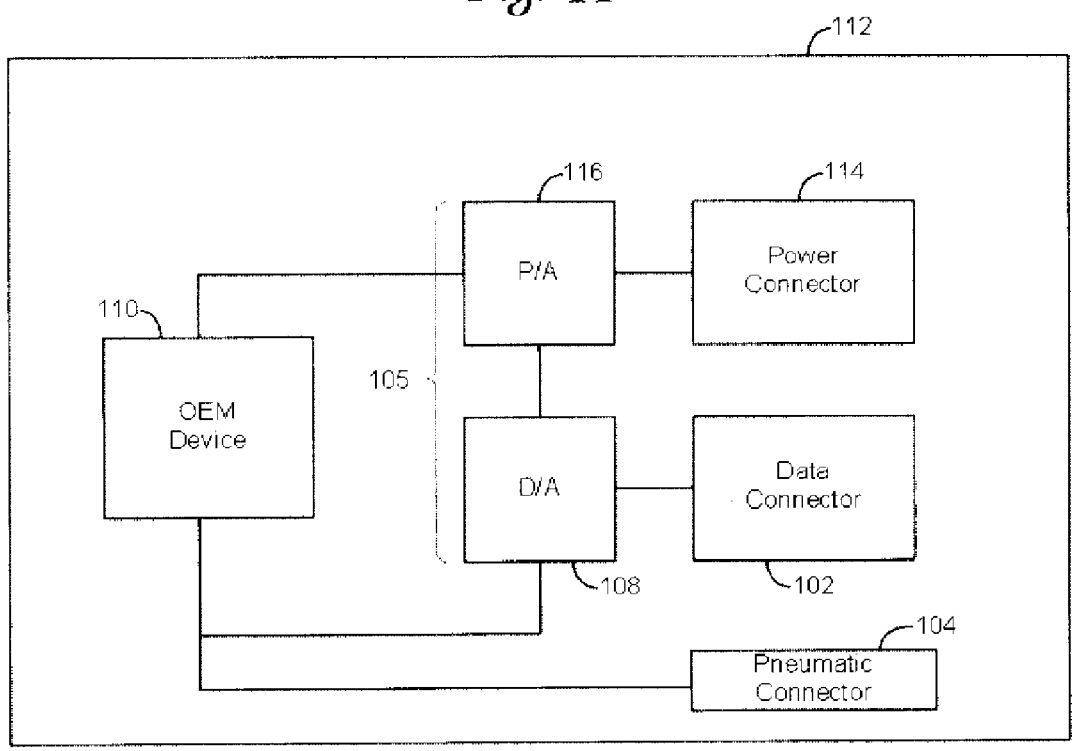
FIG. 11 is a block diagram of the high power module.
Figure 12:
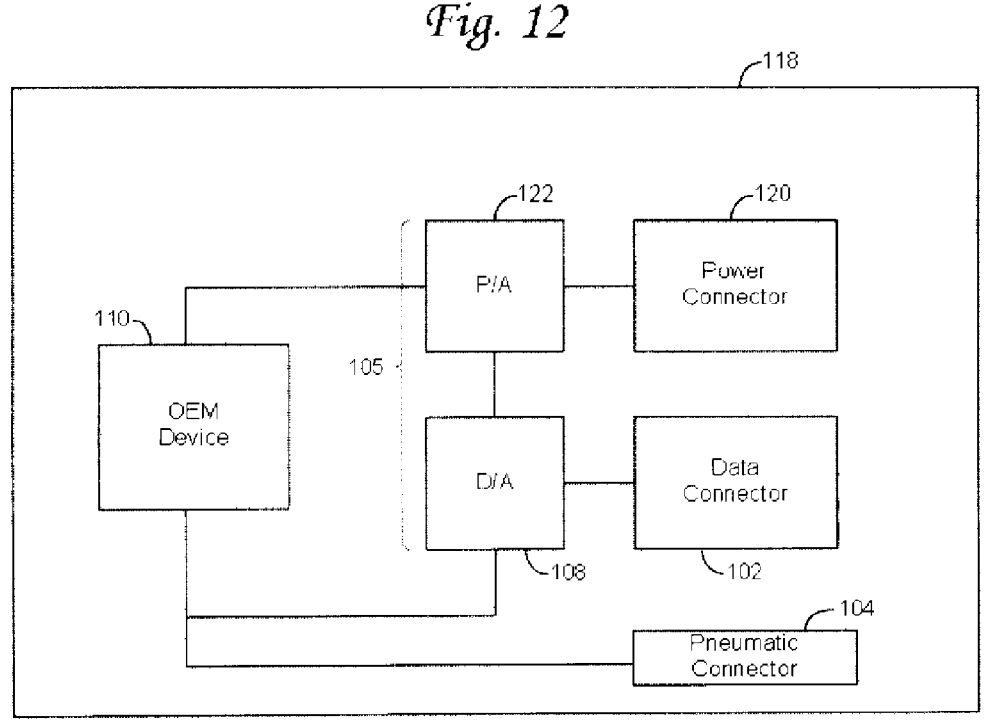
FIG. 12 is a block diagram of the low power module.

It is contemplated that one particular embodiment includes two power spines; in particular, a high power spine 23 and a low power spine 27 as is shown in FIG. 10. The low power spine 27 is responsible for providing power to the internal network populated with lower current subsystem modules 118 that require higher stability of power. The high power spine 23 is responsible for providing power for high current subsystem modules 112 separated by appropriate filtering to limit the electromagnetic effects imposed by the electromechanical components when such high current devices exist within the platform 10. The high power spine 23 includes a plurality of high power ports 25 and the low power spine 27 includes a plurality of low power ports 29. A high power module 112 includes a medical device 110 that requires high current, while a lower power module 118 includes a medical device 110 that requires lower current than the medical device 110 in the high power module 112.

The high power module 112 receives power from the high power spine 23 and includes a high power connector 114 which is connectable to the high power ports 25. A high power adapter 116 receives the power and coverts the power according to the requirements of the corresponding medical device 110. A low power module 118 receives power from the low power spine 27 and includes a low power connector 120 which is connectable to the low power ports 29. A low power adapter 122 receives the power and converts the power according to the requirements of the corresponding medical device 110. The high power and low power spines 23, 27 provide a reasonable division of power between the high power and low power modules 112, 118. However, it should be noted that two power spines are not required for modules 12 having different power requirements but may be desirable in certain implementations of the present invention.

In addition to providing centralized power, the control spine 15 may also be configured to provide centralized data communication. Therefore, one embodiment of the control spine 15 includes a data spine 26. The data spine 26 is a central data distributor among the various components of the platform 10. Data may be communicated along the data spine 26 in a common data language. Alternatively, data communicated to each module 12 may be tailored to the specific data requirements of the specific module 12. The data spine 26 includes a plurality of data ports 28 which are connectable to the modules 12. The data ports 28 enable quick and easy module 12 connection to the data spine 26.

In one implementation of the invention, the modules 12 include a data connector 102 that is connectable to a data port 28 to enable data communication between the data spine 26 and the module 12. With regard to a data spine 26 which employs a common data language, it is understood that the medical device 110 may not understand such a common data language. Therefore, the module 12 may include a data adapter 108 which translates the data between the data spine 26 and the medical device 110. In this regard, the data adapter 108 is in electrical communication with the data connector 102 and the medical device 110. Data communicated from the data spine 26 to the medical device 110 is translated from the common data language into a language understandable by the medical device 110, referred to herein as the medical device language. Conversely, data communicated from the medical device 110 to the data spine 26 is translated from the medical device language into the common data language. The medical device language may vary among the medical devices 110. Therefore, each data adapter 108 may be tailored to a corresponding medical device 110. The data adapter 108 enables compatibility between the data spine 26 and the medical device 110. Without the data adapter 108, the medical device 110 may not be able to communicate with the data spine 26. The data adapter 108 and/or power adapter 106 may define a module translator 105.

Another aspect of the present invention includes a central pneumatic spine 30. The pneumatic spine 30 enables fluid transfer within the platform 10, which is required for a number of different medical treatments and therapies. The pneumatic spine 30 includes a plurality of pneumatic ports 32 that are connectable to the modules 12. A pneumatic control unit controls the communication of fluid along the pneumatic spine 30. A pump or fan may force fluid flow along the pneumatic spine 30. In this regard, the control unit may control the amount of fluid flow forced by the pump or fan. The pneumatic spine 30 may include a filter 80 in fluid communication therewith to remove contaminants from the fluid traveling along the pneumatic spine 30. Each module 12 requiring connection to the pneumatic spine 30 includes a pneumatic connector 104 that is connectable to the pneumatic ports 32.

A fluid source may be in fluid communication with the pneumatic spine 30. Fluid from the fluid source may flow along the pneumatic spine 30 to the modules 12 or to a pneumatic port 50. Such a fluid source may include, but is not limited to an oxygen source 78, an oxygen generator 76, an oxygen port 74 or other fluids known by those skilled in the art.

As stated above, each module 12 may include power, data and pneumatic connectors 100, 102, 104 that are connectable to power, data and pneumatic ports 24, 28, 32, respectively. In one embodiment, the modules 12 are hot-swappable to enhance the flexibility and adaptability of the platform 10. In other words, modules 12 may be added or removed while the platform 10 is powered on without loss of data or damage to the platform 10 or module 12. In this regard, the size of the power, data, and pneumatic connectors 100, 102, 104 is substantially the same in different modules 12. This commonality permits quick and easy addition or removal of a module 12 without much effort to enable modification of the medical functionality on-the-fly.

The platform 10 may provide automatic detection of changes in module 12 configuration, including additions, deletions or upgrades. Upon detection of module 12 changes, the platform 10 may automatically provide appropriate control and display capabilities needed to access the capabilities found to be present. Preferably, the platform 10 provides controls and displays for only those modules 12 that have been detected as being integrated into the platform 10.

The operational instructions for power, data, and pneumatic control may be input by a user or they may be preprogrammed into the power, data, and pneumatic control units, collectively referred to as the control unit 90. In another embodiment, the control unit 90 may contain preset operational instructions for multiple operating modes. In that case, a user simply inputs an operating mode and the control unit 90 communicates corresponding operational instructions to the appropriate modules 12.

As mentioned above, the medical functionality is easily adaptable by adding or removing modules 12. As modules 12 are connected to the platform 10, corresponding apparatus ports 50, 48 may be required. Therefore, in one embodiment of the invention, the patient interface panel 46 is reconfigurable to tailor the apparatus ports 48, 50 to correspond to the connected modules 12. As such, both treatment and pneumatic ports 48, 50 may be reconfigured as needed.

Another important aspect of many treatments and therapies is an oxygen supply. One embodiment of the invention includes an internal oxygen supply 78. The oxygen supply 78 is in fluid communication with the pneumatic spine 30 to enable transfer and delivery of the oxygen. The oxygen supply 78 is stored in an oxygen bay within the housing 14. In another embodiment of the invention there is included an internal oxygen generator 76 in fluid communication with the pneumatic spine 30. The oxygen generator 76 is capable of producing medical grade oxygen to the patient via the pneumatic spine 30. In an alternate embodiment, oxygen is supplied via an external oxygen source. The external oxygen source is connectable to the pneumatic spine 30 via an external oxygen port 74. It may be desirable to obtain oxygen from an external supply when there is no internal supply 78, or to preserve an internal supply 78.

In one embodiment of the invention, commands and/or data executed and gathered during medical treatment and therapy are stored by a data logger 94. The data logger 94 may be in electrical communication with the data and/or power spines 26, 22. According to one embodiment of the invention, the data logger 94 includes storage capacity to support a long endurance care scenario including initial stabilization, ground transport, staging, in-theatre evacuation, staging, and CONUS (continental United States) evacuation. The data logger 94 may maintain all information monitored by the modules 12, including physiological data, therapeutic events, annotations, alarms, and environmental information. According to one embodiment, the data logger 94 is capable of storing such information, without loss, for a minimum of a seventy-two hour period. In one implementation, the control spine 15 is able to retrieve data from the data logger 94. Such data may be useful in determining a particular treatment or therapy for a patient. The data logger 94 may additionally be in electrical communication with the power spine 22 to record the power levels thereof. Data recording may be accomplished through the use of flash multi-media cards, compact flash, or other similar devices. Data may also be recorded by external storage devices, such as a USB disk drive. In one embodiment of the invention, under low internal power source conditions or a warning of system power down, the modules 12 will enter a FAILSAFE mode where logging of information is stopped, and all necessary information is saved to secondary storage. According to one embodiment, prior to a loss of power to a module 12 or the platform 10 as a whole, all information that is required for the next usage of the platform 10 may be stored into a non-volatile memory to allow future recovery of all information intended for storage, and for restoration of equipment to same operational state upon next power-up.

To assist in the examination of patient data, one embodiment of the present invention includes a data analyzer 93 operative to present a care-giver a summery of logged patient data. The data analyzer 93 is capable of identifying markers in the data (e.g., voice annotations, markers, drug administration changes, etc.) to help guide the analysis. In one embodiment, the data analyzer 93 allows a minimum of twenty-four hours of data to be viewed. The data analyzer 93 may allow parameters to be correlated with each other. In addition, the data analyzer 93 may be capable of exporting the data to external applications for further analysis. The data analyzer 93 may be in electrical communication with the data and/or power spines 26, 22.

In one embodiment of the invention, there is included a power management unit 92 to monitor the power supply and consumption by the platform 10. The power management unit 92 is in electrical communication with the power and data spines 22, 26. When no external power source is available, the power management unit 92 directs the internal power source to supply power to the power spine 22. According to one particular implementation, the internal power source is capable of providing power to the platform 10 to allow it to operate for a period of at least sixty minutes when fully charged. In order to allow the platform 10 to operate on internal power for extended periods of time, the platform 10 may include multiple internal power sources, such as multiple batteries. To optimize the usage of the internal power sources, one source at a time may be utilized to power the platform 10 until that source has been discharged. The power management unit 92 may also monitor the charge state of the internal power source. Proper management of the internal power source is essential to optimize performance and usage thereof. This includes providing the ability to control the charging of the internal power sources. As part of this goal, the platform 10 may include a charger. Further, to allow users to optimize internal power source management on an installation-by-installation basis, it is desirable to provide the ability to prioritize the order in which the internal power sources are charged. While it may be desirable to charge the internal power sources any time the platform 10 is powered by an external source, the power management unit 92 may preclude any internal power source charging when medical equipment is operating to ensure peak current limits are not exceeded. Trickle charging may be possible when only a subset of medical equipment is operating.

According to one embodiment, the platform 10 complies with applicable FDA and/or European regulatory alarm requirements. The platform 10 may provide both auditory and visual alarms approximately five minutes in advance, and continuously thereafter, to indicate imminent loss of battery power. The platform 10 may automatically discontinue the power-failing alarm upon addition of sufficient battery capacity, or connection to a compatible external power source.

It is contemplated that one embodiment of the platform 10 includes an alarm management unit 96 in electrical communication with the data and power spines 26, 22. The alarm management unit 96 communicates an alarm signal when patient data is equal to at least one alarm limit. As used herein, the alarm limit is a condition, level, or unit of time that may be set by a user, or included in pre-programmed instructions. In this regard, the alarm management unit 96 alerts an operator when the patient data equals the alarm limit.

The platform 10 may operate in a wide range of environments and temperatures. Consequently, the ambient air temperature as well as heat-generating electronics within the platform will cause heat to build up. As such, one embodiment of the invention includes an environmental control unit 52 disposed within the housing 14. The environmental control unit 52 controls the heating and cooling within the housing 14 to maintain an operable temperature. The environmental control unit 52 includes a temperature sensor 54 to monitor the temperature within the housing 14. The temperature sensor 54 is in electrical communication with an environmental control circuit 56 which communicates operational instructions to a fan 58. The fan 58 forces air-flow through the housing 14 to control the temperature. The environmental control unit 52 is capable of performing automatic environmental control to provide thermal cooling or heating that will only operate when internal temperatures exceed a desired operating threshold limit, and will automatically shutoff when internal temperatures return within the desired operating range. The operational and shutoff (on/off) thresholds are controllable to allow a user to set the threshold temperature at which the heating/cooling turns on (becomes operational), and the threshold temperature at which the heating/cooling turns off (shutoff). Under high or extreme low temps, the fan 58 will operate to force outside air through the platform 10. The platform 10 will remove heat by transferring the thermal energy into the air-stream and out of the platform 10. The modules 12 are sealed, and conduct heat to the module casing. The air will pass over the modules 12 to remove heat. In extreme cold, the same process will be used to warm the unit (assuming the air outside the unit is warmer than the interior).

In addition to the foregoing, it is expressly contemplated that the present invention may find widespread applicability as a lightweight, portable medical treatment device. In one embodiment, the device is a smaller version of the platform 10 described above. In particular, the device does not include a patient support surface 16. Such a device may include wheels attached to the bottom of the housing to enable easy transport of the device. In addition, straps or handles may also be included to facilitate transportation. In this regard, the device provides high-level medical functionality that is extremely portable and adaptable to a particular patient's situation.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A patient care and treatment platform being connectable to a plurality of medical modules, each medical module being configured to provide discrete medical functionality, the platform comprising:

a housing having a patient support surface disposed on the housing, the patient support surface being configured to support a patient thereon, the housing configured to receive a plurality of the medical modules below the patient support surface with at least one of the modules in communication with detachable sensors adapted for placement on a patient during use or detachable patient treatment devices for patient treatment during use;

a control spine connected to the housing and extending along a centrally located length of the housing and below the patient support surface, the housing configured to receive modules disposed on opposing sides of the housing and opposing sides of the spine, the control spine having a plurality of control ports along a length of the spine, each control port being configured to enable selective attachment/detachment to a respective one of the plurality of medical modules to enable centralized control over the plurality of modules, the control spine including a control unit configured to transmit control communications and sensor communications along the control spine during use, the control unit being configured to detect attachment/detachment of the modules to/from the control spine and to provide control capabilities needed to access the functionalities detected; and a patient interface panel connected to the housing, the patient interface panel having a plurality of treatment ports, each treatment port being connectable with a respective one of the plurality of medical modules and a treatment apparatus through the control spine during use.

2. The platform of claim 1, wherein the housing includes a head fairing having a bottom surface abutting the patient support surface, a top surface in parallel spaced relation to the bottom surface, and a sloped, arcuate inner surface extending from the top surface to the bottom surface for accessing a head of a patient.

3. The platform of claim 2, wherein the patient interface panel is disposed on the head fairing.

4. The platform of claim 1, further comprising a user interface connected to the housing and in electrical communication with the control spine, the user interface being operative to enable operator control over the modules.

5. The platform of claim 4, wherein the user interface includes a button-wheel selector to enable the operator to input operator instructions into the control spine.

6. The platform of claim 1, further comprising a handle connected to the housing to facilitate transport of the platform.

7. The platform of claim 6, wherein the handle includes a receptacle portion and a body portion, the receptacle portion being connected to the housing, wherein the body portion is retractably connected to the receptacle portion.

8. The platform of claim 1, wherein at least one of the plurality of treatment ports is an electronic treatment port being electrically connectable to a respective one of the plurality of medical modules and an electronic treatment apparatus.

9. The platform of claim 1, wherein at least one of the plurality of treatment ports is a pneumatic treatment port being fluidly connectable to a respective one of the plurality of medical modules and a pneumatic treatment apparatus.

10. The platform of claim 1, further comprising a patient support surface disposed on the housing, the patient support surface being configured to support a patient thereon.

11. The platform of claim 1, further comprising a power receiver connected to the housing and in electrical communication with the control spine, the power receiver being operative to receive power from a power source.

12. The platform of claim 1, further comprising an environmental control unit disposed within the housing, the environmental control unit being operative to control the heating and cooling within the housing, the environmental control unit comprising:

a temperature sensor to monitor the temperature within the housing;

an environmental control circuit in electrical communication with the temperature sensor; and a fan in electrical communication with the environmental control circuit, the fan being operative to force air-flow within the housing to control the temperature within the housing, wherein the fan is responsive to operational instructions communicated from the environmental control circuit.

13. The platform of claim 1, wherein the patient interface panel is re-configurable to provide treatment ports which correspond to medical modules connected to the platform.

14. The platform of claim 1, further comprising a display in electrical communication with the plurality of modules, the display being operative to display patient data.

15. The platform of claim 1, further comprising a comfort pad disposed on the patient support surface.

16. The platform of claim 1, wherein the control spine is a data control spine, the control unit being operative to transmit data communications along the data control spine.

17. The platform of claim 1, wherein the control spine is a power control spine, the control unit being operative to transmit power communications along the power control spine.

18. The platform of claim 1, wherein the control spine is a fluid control spine, the control unit being operative to transmit fluid communications along the fluid control spine.

19. The platform of claim 1, wherein each control port is configured to enable selective attachment/detachment to a respective one of the plurality of medical modules during platform operation.

20. The platform of claim 1, wherein each medical module defines an operational parameter, the operation of each medical module being dependent upon the operational parameter being satisfied, the control spine being configured to detect the respective operational parameter of at least one of the plurality of medical modules attached to the control spine and to adapt the control communications to meet the operational parameters of the medical modules.

21. A patient care and treatment platform comprising:

a housing having an elongated portion on which the patient can be placed during use;

a control spine connected to the housing and extending along a center of the elongated portion of the housing, the control spine having a plurality of control ports on opposing sides of the control spine, the control spine including a control unit configured to transmit control communications along the control spine during use; and at least one medical module being selectively attachable/detachable to the control spine, the at least one medical module including:

a module housing;

a medical device disposed within the module housing, the medical device being configured to perform medical functionality and generating patient data;

an adaptive interface being connectable to one of the plurality of control ports; and a module translator associated with each medical device, the module translator being in communication with the adaptive interface and the medical device, the module translator being operative to adapt the communications received from the control network to the operational requirements of the medical device;

wherein the control unit is configured to regulate the control communications in response to the patient data generated by the medical device.

22. The platform of claim 21, wherein the housing includes a head fairing having a bottom surface abutting the patient support surface, a top surface in parallel spaced relation to the bottom surface, and a sloped, arcuate inner surface extending from the top surface to the bottom surface for accessing a head of a patient.

23. The platform of claim 22, wherein the patient interface panel is disposed on the head fairing.

24. The platform of claim 21, further comprising a patient interface panel connected to the housing, the patient interface panel having a plurality of treatment ports, each treatment port being connectable with a respective one of the plurality of medical modules.

25. The platform of claim 21, further comprising a patient support surface disposed on the housing, the patient support surface being configured to support a patient thereon.

26. The platform of claim 21, wherein the at least one medical module is selectively attachable/detachable to the control spine during platform operation.

* * * * *